(12) United States Patent
Werner et al.

(10) Patent No.: US 6,194,179 B1
(45) Date of Patent: Feb. 27, 2001

(54) METHOD FOR PREPARING POLYNUCLEOTIDE SEQUENCES AND USES THEREOF

(75) Inventors: Milton H. Werner; Vineet Gupta, both of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/357,541

(22) Filed: Jul. 20, 1999

(51) Int. Cl.[7] .............................. C12D 19/34; C12Q 1/68; G01N 33/00; C07H 21/02; C07H 21/04
(52) U.S. Cl. .................... 435/91.2; 435/6; 435/91.1; 436/94; 536/23.1; 536/24.33
(58) Field of Search ............................ 435/6, 91.1, 91.2, 435/183; 536/23.1, 24.3, 24.33, 25.3; 436/94

(56) References Cited

PUBLICATIONS

Louis et al., Preparation of uniformly isotope–labeled DNA oligonucleotides for NMR spectroscopy. J. Biol. Chem. 273, 2374–2378, Jan. 1998.*

Chen et al., A PCR–based method for uniform 13C/15N labeling of long DNA oligomers. FEBS Letters 436, 372–376, Oct. 1998.*

White et al., Concatemer Chain Reaction: A Taq DNA polymerase–mediated mechanism for generating long randemly repetitive DNA sequences. Anal. Biochem. 199, 184–190, 1991.*

Hemat et al., A rapid and efficient PCR–based method for sythesizing high–molecular–weight multimers of oligonucleotides. Biochem. Blophys. Res. Commun. 205, 475–481, 1994.*

Van Ness et al., A versatile solid support system for oligonucleotide probe–based hybridization assays. Nucleic Acids Res. 19, 3345–3350, 1991.*

Zimmer et al., NMR of enzymatically synthesized uniformly 13C 15N –labeled DNA oligonucleotides. Proc. Natl. Acad. Sci. USA 92, 3091–3095, 1995, 1991.*

Chen et al., 1998, FEBS Letter 436:372–6.

Hemat et al., 1994, Biochem. Biophys. Res. Comm. 205:475–81.

Louis et al., 1998, J. Biol. Chem. 273:2374–8.

Masse et al., 1998, J. Nucleic Acids Res. 26:2618–24.

Rudert et al., 1990, Nucleic Acids Res. 18:6460.

Smith et al., 1997, J. Biomol. NMR, 10:245–53.

White et al., 1991, Analytical Biochem. 199:184–90.

\* cited by examiner

Primary Examiner—Bradley L. Sisson
Assistant Examiner—Frank Lu
(74) Attorney, Agent, or Firm—Klauber & Jackson

(57) ABSTRACT

Methods are described for the preparation of quantities of preselected polynucleotide sequences in purified form. The method is independent of length or sequence, and can be used to prepare multi-milligram quantities of, for example, single length, isotope-enriched duplex DNA following a single-step chromatographic purification of the desired product. The method of the present invention allows for preparative scale synthesis of DNA yielding a single product length. The application of the method to NMR spectroscopy of DNA provides the opportunity to identify biologically relevant interactions between polynucleotide sequences and other macromolecules, and assist in the identification and development of agents having therapeutic utility as a consequence of the promotion or antagonism of these interactions.

14 Claims, 11 Drawing Sheets

21kbp
7.4kbp
5.7kbp
3.5kbp 2  4  6

2  4  6

SEQUENCE LISTING

```
<160> NUMBER OF SEQ ID NOS: 12

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 1
atcaggatgc ggttactgat atcaggatgc ggttactgat                           40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 2
atcagtaacc gcatcctgat atcagtaacc gcatcctgat                           40

<210> SEQ ID NO 3
<211> LENGTH: 20
<212> TYPE: DNA
<213> ORGANISM: Artificial Sequence
```

```
<220> FEATURE:
<223> OTHER INFORMATION: Description of Artificial Sequence:synthetic;
      related to mouse

<400> SEQUENCE: 3
atcaggatgc ggttactgat                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 4
atcagtaacc gcatcctgat                                                    20

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 5
atccagagga tgtggcttct gatatccaga ggatgtggct tctgat                       46

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 6
atcagaagcc acatcctctg gatatcagaa gccacatcct ctggat                       46

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 7
atccagagga tgtggcttct gat                                                23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 8
atcagaagcc acatcctctg gat                                                23

<210> SEQ ID NO 9
<211> LENGTH: 26
<212> TYPE: DNA
<213> ORGANISM: Artificial Sequence
<220> FEATURE:
```

```
<223> OTHER INFORMATION: Description of Artificial Sequence:synthetic;
      related to mouse

<400> SEQUENCE: 9
atcgtttgtc gatatcgttt gtcgat                                          26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 10
atcgacaaac gatatcgaca aacgat                                          26

<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 11
atcgtttgtc gat                                                        13

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence:synthetic;
      related to mouse

<400> SEQUENCE: 12
atcgacaaac gat                                                        13
```

METHOD FOR PREPARING POLYNUCLEOTIDE SEQUENCES AND USES THEREOF

FIELD OF THE INVENTION

The present invention relates to methods for the preparation of quantities of substantially pure polynucleotide sequences, which may be isotopically enriched. Such sequences may be used for therapeutic purposes, for the identification of interactions between the polynucleotide sequences and proteins or other binding partners, and to identify agents which modulate these interactions.

BACKGROUND OF THE INVENTION

Since the advent of DNA thermal amplification technology, numerous procedures have been developed to amplify polynucleotide sequences on a preparative scale. Of these, the concatamer chain reaction developed independently by Rudert et al. (17a) and White et al. (17b) employ a DNA polymerase-catalyzed thermal amplification system for the generation of DNA concatamers. In this procedure, the primer and template for the amplification reaction are the identical molecule, producing large sequences comprising tandem repeats of the target DNA sequence. Following similar procedures, Louis et al. (17c) prepared isotopically-labeled DNA oligonucleotides for NMR spectroscopy, utilizing labeled deoxynucleotide triphosphates. Although the lafter procedure produced oligonucleotides, amounts of product are still limited and restrict the utility of subsequent studies requiring larger quantities of oligonucleotides. Furthermore, these procedures introduce a degree of heterogeneity in the product, making it unsuitable for certain uses, in particular, high resolution heteronuclear NMR spectroscopy.

Multi-dimensional heteronuclear NMR has become a standard technique to determine the three-dimensional structure of proteins and RNA in solution (1,2). One of the most important advances in the application of NMR spectroscopy to the study of biological systems has been the ease of incorporation of $^{13}$C and/or $^{15}$N into proteins (2–5) and RNA.(6–8). The enrichment of macromolecules in these stable isotopes allows for the dispersion of $^{1}$H, $^{13}$C and $^{15}$N chemical shifts into multiple spectral dimensions in a manner that preserves the chemical and/or spatial relationship between atoms within a molecule of interest (2–5). The resulting enhancement of spectral sensitivity and resolution has had a tremendous impact on the study of chemical and biological phenomena of proteins and RNA. (2–8). In contrast, both the detailed analysis of structure and dynamics of DNA in solution have remained largely inaccessible to the NMR spectroscopist despite the ease of preparation of oligonucleotide duplexes of biological interest. Poor proton density and narrow chemical shift dispersion limits the detailed analysis of structural parameters by homonuclear $^{1}$H-NMR to very small oligonucleotides. While it is desirable to apply heteronuclear NMR to the study of DNA in solution, it has required de novo synthesis of DNA precursors for solid-phase synthesis (9–11). These methods require a certain level of synthetic expertise and are both cost and labor intensive. In this regard, an enzymatic approach would be advantageous and a few such methods have been proposed in recent years (12–17).

It is towards the improvement in the quantity and quality of the large scale preparation of polynucleotide sequences, and in particular, isotopically enriched polynucleotide sequences, and uses thereof, that the present invention is directed.

The citation of any reference herein should not be construed as an admission that such reference is available as "Prior Art" to the instant application.

SUMMARY OF THE INVENTION

In its broadest aspect, the present invention is directed to a method for preparing a quantity of a preselected polynucleotide sequence which is flanked by half sequence-specific endonuclease sites, following the steps of (1) preparing an amplification template/primer comprising at least one tandem repeat of the preselected polynucleotide sequence separated by a full sequence-specific endonuclease site and flanked by half endonuclease sites; (2) amplifying the template/primer by a DNA polymerase-catalyzed thermal amplification reaction in a first step utilizing an optimized annealing temperature; (3) further amplifying the product of the previous step by a DNA polymerase-catalyzed thermal amplification reaction utilizing an optimized annealing temperature; and (4) cleaving the product of the previous reaction using the endonuclease, producing the preselected polynucleotide sequence. To enhance the quantity of product produced by the above reaction, a quantity of the preselected polynucleotide sequence may be included in the second amplification step.

The template/primer for the above-described procedures comprises at least one tandem repeat of the preselected polynucleotide sequence. It may be prepared by solid-phase phosphoramidite chemistry. The preselected polynucleotide sequence may be, by way of non-limiting example, duplex DNA, single-stranded DNA, triplex DNA, quadruplex DNA, 3-way junction DNA, or 4-way junction DNA. The half endonuclease sites on the template/primer may be blunt-ended or overhanging. Additional endonuclease sites may be included in the template/primer such that selective cleavage after amplification may be used to generate quantities of particular sequences.

To prepare a quantity of an isotopically enriched polynucleotide sequence, the deoxynucleotide triphosphates used in the amplification steps are isotopically enriched. To enhance the quantity of isotopically enriched product, a quantity of the preselected polynucleotide sequence may be included in the second amplification step. This added preselected polynucleotide sequence may or may not be isotopically enriched. Non-limiting examples of isotopically enriched atoms of the deoxynucleotide triphosphates include $^{13}$C, $^{15}$N, $^{2}$H, and any combination thereof.

The optimal annealing temperature of the first amplification step of the above process is selected by determining an annealing temperature which yields a maximal amount of endonuclease-cleaved preselected polynucleotide sequence as a product of the first amplification step. Likewise, the optimized annealing temperature of the second amplification step is selected by determining an annealing temperature which yields a maximal amount of endonuclease-cleaved preselected polynucleotide sequence as a product of the second amplification step.

To prepare isotopically enriched deoxynucleotide triphosphates, enzymatic phosphorylation of deoxynucleotide phosphates may be obtained for example by digestion of nucleic acid isolated from an organism grown on an isotopically enriched carbon source, an isotopically enriched nitrogen source, or the combination of the two. Other isotopically enriched sources may be utilized to provide other isotopically enriched atoms. In one non-limiting example, nucleotide phosphates isolated from an organism may be enzymatically phosphorylated using suitable enzymes in combination with thymidylate monophosphate kinase (TMPK) and cytidylate monophosphate kinase (CMPK).

In a second aspect of the present invention, a method is provided for preparing a quantity of a substantially pure, preselected polynucleotide sequence which is flanked by half sequence-specific endonuclease sites, following the steps of (1) preparing an amplification template/primer comprising at least one tandem repeat of the preselected polynucleotide sequence separated by a full sequence-specific endonuclease site and flanked by half endonuclease sites; (2) amplifying the template/primer by a DNA polymerase-catalyzed thermal amplification reaction in a first step utilizing an optimized annealing temperature; (3) further amplifying the product of the previous step by a DNA polymerase-catalyzed thermal amplification reaction utilizing an optimized annealing temperature; (4) cleaving the product of the previous reaction using the endonuclease, producing the preselected polynucleotide sequence; and (5) isolating the preselected polynucleotide sequence from the previous step. Isolation may be carrier out in a single-step chromatographic procedure, for example, using DEAE ion-exchange HPLC.

In a further aspect of the present invention, a method for preparing a quantity of a substantially pure, isotopically enriched preselected polynucleotide sequence is provided, the preselected polynucleotide sequence which is flanked by half sequence-specific endonuclease sites, following the steps of (1) preparing an amplification template/primer comprising at least one tandem repeat of the preselected polynucleotide sequence separated by a full sequence-specific endonuclease site and flanked by half endonuclease sites; (2) amplifying the template/primer by a DNA polymerase-catalyzed thermal amplification reaction in a first step in the presence of isotopically-enriched deoxynucleotide triphosphates, utilizing an optimized annealing temperature; (3) further amplifying the product of the previous step by a DNA polymerase-catalyzed thermal amplification reaction in the presence of isotopically-enriched deoxynucleotide triphosphates, utilizing an optimized annealing temperature; (4) cleaving the product of the previous reaction using the endonuclease, producing the preselected polynucleotide sequence; and (5) isolating the preselected polynucleotide sequence from the previous step. Isolation may be carrier out in a single-step chromatographic procedure, for example, using DEAE ion-exchange HPLC.

In yet a further aspect of the present invention, a method is provided for identifying a protein binding site on a preselected polynucleotide sequence comprising the steps of: (1) preparing an isotopically enriched preselected polynucleotide sequence in accordance with the above-described procedure; (2) conducting NMR spectroscopy with a mixture of the preselected protein and the preselected polynucleotide sequence; (3) detecting chemical shift perturbations between free and bound states at specific reporter atoms in the preselected polynucleotide sequence; and (4) correlating the perturbations with the presence of a protein binding site between the preselected protein and the preselected polynucleotide sequence.

The present invention is yet further directed to methods for identifying agents capable of modulating the interaction between a preselected protein and a preselected polynucleotide sequence by carrying out the following steps: (1) preparing an isotopically enriched preselected polynucleotide sequence in accordance with the above-described procedure; (2) conducting NMR spectroscopy with a mixture of the preselected protein and the preselected polynucle-otide sequence in the absence and presence of an agent; (3) detecting changes in chemical shifts between free and bound states at specific reporter atoms in the preselected polynucleotide sequence as a consequence of the presence of the agent; and (4) correlating any changes detected as a consequence of the presence of the agent with the modulating by the agent of the interaction between the preselected protein and the preselected polynucleotide sequence. The agent may antagonize or promote the interaction between the preselected protein and the preselected polynucleotide sequence.

In still yet a further aspect of the present invention, the procedure for preparing a quantity of a substantially pure, preselected polynucleotide sequence may be used to prepare therapeutically effective amounts of antisense oligonucleotides.

These and other aspects of the present invention will be better appreciated by reference to the following drawings and Detailed Description.

BRIEF DESCRIPTION OF THE DRAWINGS

FIG. 3B indicates that the duplex products are single length. The trace amount of DNA seen as a doublet in each lane is a small amount of denatured duplex formed during electrophoresis.

DETAILED DESCRIPTION OF THE INVENTION

Figure 1A:
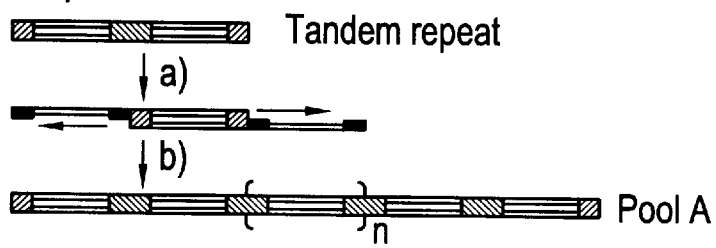
FIG. 1A depicts schematically the amplification reactions of the present invention. The first prepares a self-priming/self-propagating template pool and the second step synthesizes long, tandemly-repeated DNA.
Figure 1A:
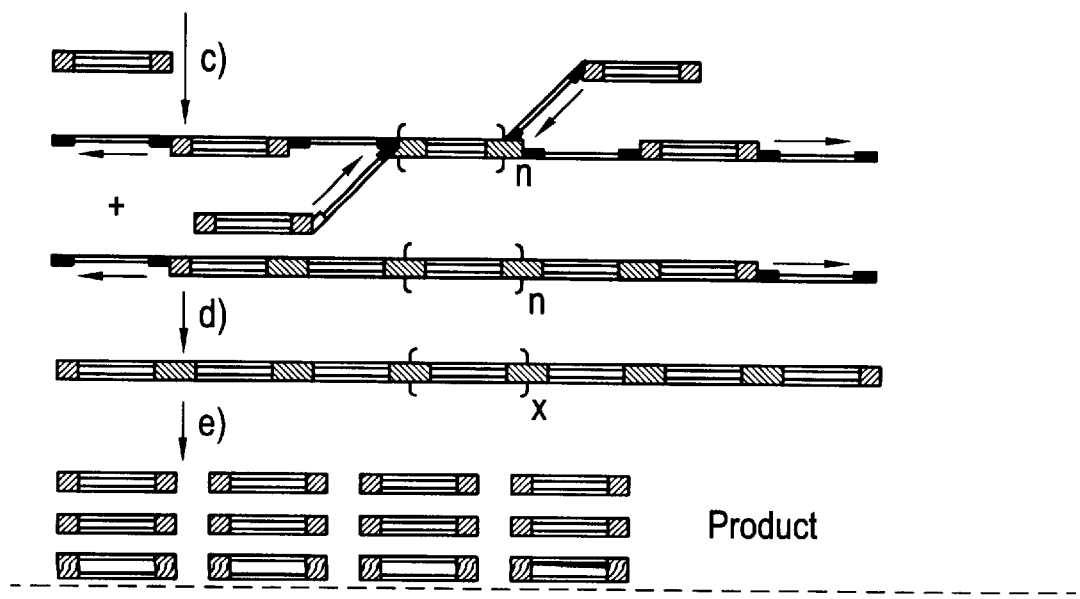

The methods described herein for the preparation of a quantity of a preselected polynucleotide sequence is an enzymatic approach to polynucleotide synthesis which overcomes many of the shortcomings of earlier methods. Multi-milligram quantities of, for example, single length, isotope-enriched duplex DNA can be prepared by this method with product to template/primer yields of equal to or greater than about 800:1 following a single-step chromatographic purification of the desired product. Being neither sequence nor length dependent, the method of the present invention allows for preparative scale synthesis of DNA yielding a single product length. The application of the instant method to NMR spectroscopy of DNA provides the opportunity to explore interactions between protein and polynucleotides. The instant method has enabled the acquisition of previously inaccessible information at the protein/DNA interface in solution, such as the first evidence of hydrogen-bonding between a protein and DNA. Thus, the quantity and quality of the isotopically enriched polynucleotide sequence produced herein is sufficient such that it may be used to identify biologically relevant interactions between polynucleotide sequences and other macromolecules, and assist in the identification and development of agents having therapeutic utility as a consequence of the promotion or antagonism of these interactions.

The method of the present invention provides for preparing a quantity of a preselected polynucleotide sequence, said preselected polynucleotide sequence flanked by half of a sequence-specific endonuclease site, comprising the steps of:

a. preparing an amplification template/primer comprising at least one tandem repeat of said preselected polynucleotide sequence separated by a full sequence-specific endonuclease site and flanked by half of a sequence-specific endonuclease site;

b. amplifying said template/primer by a DNA polymerase-catalyzed thermal amplification reaction in a first step comprising deoxynucleotide triphosphates, and producing a first product, said first step utilizing an optimized first annealing temperature for said preselected polynucleotide sequence;

c. amplifying said first product by a DNA polymerase-catalyzed thermal amplification reaction in a second step comprising deoxynucleotide triphosphates, and producing a second product, said second step utilizing an optimized second annealing temperature for said preselected polynucleotide sequence; and d. cleaving said second product using said at least one endonuclease, producing said preselected polynucleotide sequence.

The starting reagent for the amplification is at least one tandem repeat of target polynucleotide sequence, providing an enzymatic template which is both self-priming and self-propagating. The sequence may be prepared, by way of a non-limiting example, using solid-phase phosphoramidite chemistry. The tandem repeat is separated and flanked on each end by a cleavage site for a sequence-specific endonuclease, which may be blunt-ended or overhanging. As noted above, the tandem repeats serve both as primers and templates for a DNA polymerase-catalyzed thermal amplification reaction, and thus is referred to herein as the template/primer. The first amplification step in the instant method creates a template/primer pool (Pool A of FIG. 1A) using the tandem repeat duplex and deoxynucleotide triphosphates (dNTPs). dNTPs may be prepared, for example, from the genomic DNA of a microorganism; for the preparation of isotopically enriched polynucleotides, isotopically enriched deoxynucleotide triphosphates prepared from genomic DNA from a microorganism grown on isotopically enriched compounds may be utilized. Pool A is distributed in a second step to a series of identical reactions to initiate self-propagating DNA polymerization resulting in a large DNA product pool with average lengths that may be in excess of 40 kilobasepairs. The overall yield of product DNA can be augmented in Step 2 by the addition of a small quantity of single repeat DNA; by way of example, about 0.5 mol %. The single repeat can be derived from Step 1 by endonuclease cleavage or it can be prepared from DNA following endonuclease cleavage of the starting primers. As the single repeat DNA represents only a small fraction of the total product, the utilization of unlabeled DNA for this purpose does not dilute the overall level of isotope-enrichment.

An important feature of the present invention is the enhancement of amplification conditions by optimizing the annealing temperature in each of the two serial synthetic thermal amplification reactions. The annealing temperature of the first amplification step of the above process is selected by determining an annealing temperature which yields a maximal amount of endonuclease-cleaved preselected polynucleotide sequence as a product of the first amplification step. Likewise, the optimized annealing temperature of the second amplification step is selected by determined an annealing temperature which yields a maximal amount of endonuclease-cleaved preselected polynucleotide sequence as a product of the second amplification step. The optimal annealing temperatures for the first and second steps is determined for each particular polynucleotide sequence, as it is not predictable.

As will be noted in the Examples described below, three different sequences were designed as structural targets for the study of protein/DNA interactions in solution:

TABLE 1

| DNA Template | Product Sequence |
|---|---|
| SEQ ID NO:1<br>ATCAGGATGCGGTTACTGATATCAGGATGCGGTTACTGAT | SEQ ID NO:3<br>ATCAGGATGCGGTTACTGAT |
| TAGTCCTACGCCAATGACTATAGTCCTACGCCAATGACTA<br>SEQ ID NO:2 | TAGTCCTACGCCAATGACTA<br>SEQ ID NO:4 |
| SEQ ID NO:5<br>ATCCAGAGGATGTGGCTTCTGATATCCAGAGGATGTGGCTTCTGAT | SEQ ID NO:7<br>ATCCAGAGGATGTGGCTTCTGAT |
| TAGGTCTCCTACACCGAAGACTATAGGTCTCCTACACCGAAGACTA<br>SEQ ID NO:6 | TAGGTCTCCTACACCGAAGACTA<br>SEQ ID NO:8 |
| SEQ ID NO:9<br>ATCGTTTGTCGATATCGTTTGTCGAT | SEQ ID NO:11<br>ATCGTTTGTCGAT |
| TAGCAAACAGCTATAGCAAACAGCTA<br>SEQ ID NO:10 | TAGCAAACAGCTA<br>SEQ ID NO:2 |

In accordance with the examples of the above table, of which the double-stranded DNA is referred to herein by the two SEQ ID numbers, the DNAs of SEQ ID NO:1/2, SEQ ID NO:5/6 and SEQ ID NO:9/10 yield products SEQ ID NO:3/4, SEQ ID NO:7/8 and SEQ ID NO:11/12, respectively, following endonuclease cleavage with EcoRV. As will be noted in the Examples below, these product DNAs represent binding sites for the Runt-domain of the transcription factor PEBP2/CBF (SEQ ID NO:3/4), for the ternary molecular complex of the Runt-domain and the DNA-binding domain of ETS1 (SEQ ID NO:7/8) and a generic binding site for a family of high mobility group (HMG) proteins known as the SOX proteins (SEQ ID NO:11/12; refs. 19–21). The interaction between these polynucleotides and proteins is an example of the utility of the instant invention in preparing useful quantities and qualities of polynucleotide sequences, in particular, isotopically labeled sequences, and their utility in detecting polynucleotide sequence interaction with a biologically relevant macromolecule, in this example, a protein.

As noted in the Example below, the DNA derived from the method of the present invention is of a high quality and fidelity. The product DNA from the Step 2 when analyzed by gel electrophoresis typically does not move out of a loading well of a 0.7% agarose gel. The product DNA is a colorless, highly viscous solution. Cleavage with the appropriate endonuclease, such as EcoRV in the case of the sequences noted above, results in a product of uniform length seen as a single band in a gel.

In one embodiment of the present invention, an enhancement of at least about 20% overall yield per vessel can be realized by the addition of single repeat DNA at the beginning of Step 2. As mentioned previously, for the preparation of isotopically enriched sequences, this added small amount of sequence may or may not be isotopically enriched, as it accounts for a very small fraction of product. By way of non-limiting example, the quantity used may be about 0.5 mol %.

Purification of the product sequence can be achieved by any one of a number of purification methods. One example of a single-step purification which achieves a high degree of purity of the product is preparative DEAE ion-exchange HPLC, which separates product DNA from unincorporated nucleotides. Denaturing polyacrylamide gel electrophoresis (PAGE) demonstrates that the main product peak from ion-exchange chromatography (Peak A of FIG. 2) is composed of essentially single-length duplex. Under these PAGE conditions, the two strands of the product duplex are resolved from each other in the gel. The shoulder seen in the chromatogram (peak B) appears to represent some uncut and degraded monomer fragments (lane 4). These could derive from aberrant EcoRV cleavage (so-called star activity) and/ or PCR mutagenesis which altered the restriction site sequence, precluding site-specific cleavage by the enzyme. For the preparation of single-stranded DNA, purification techniques which resolve one strand from the other, such as an affinity matrix or tagged affinity reagent complementary to the desired strand may be employed. Furthermore, and as mentioned above, the introduction of different sequence-specific endonuclease cleavage sites in the preselected polynucleotide sequence offers after amplification of the sequence the potential of preparing various particular sequences depending on the endonuclease used. For example, a tandem repeat of a polynucleotide sequence with a protein binding subsequence in the internal region which contains a particular endonuclease site may be used for amplification by the instant method by flanking the sequence with half sequences of a different endonuclease site, and preparing the tandem repeat for amplification. After amplification by the two serial steps of the instant invention, a quantity of the amplified original sequence may be purified by cleavage with the second endonuclease, and separately, a quantity of an amplified sequence comprising the protein recognition sequence at the ends of the sequence may be prepared using the first endonuclease. Other configurations of the tandem repeat sequence and the positions of the endonuclease sites may be utilized as appropriate for the preparation of various types of polynucleotide sequences and variations thereof, including but not limited to duplex DNA, single-stranded DNA, triplex DNA, quadruplex DNA, 3-way junction DNA, and 4-way junction DNA. In addition, RNA sequences and variations thereof may be prepared using the appropriate introduced cleavage sites.

The starting reagent is at least one tandem repeat of target polynucleotide sequence, which may be constructed by techniques known to one of ordinary skill in the art. For example, the polynucleotide sequence may be synthesized by using solid-phase phosphoramidite chemistry. The at least one tandem repeat is separated and flanked on each end by a site for a sequence-specific endonuclease.

As noted above, the method of the present invention is independent of the length or sequence of the preselected polynucleotide sequence. As will be noted in the Examples below, comparison of the band intensity for products SEQ ID NO:3/4 (20 mer), SEQ ID NO:7/8 (23 mer) and SEQ ID NO:11/12 (13 mer) by agarose gel electrophoresis demonstrates that overall yield of each product DNA is similar in each case. Analysis of the product DNAs by non-denaturing PAGE demonstrates that these are single length product duplexes.

An advantage of the instant method is that the unincorporated nucleotides are recyclable and may be recovered and used in subsequent reactions. This is particularly advantageous when isotopically enriched polynucleotide sequences are being prepared, as the isolated and purified deoxynucleotide phosphates are costly and inconvenient to prepare. Unincorporated nucleotides may re recovered from DEAE-HPLC as a mixture of dNMPs and dNTPs, which must be rephosphorylated prior to reuse. Desalting the nucleotide mixture by reversed-phase (RP) HPLC followed by phosphorylation enables the incorporation of recovered nucleotides into subsequent reactions. The product yield from the instant method is sensitive to the nucleotide concentration, thus a second round using recovered, re-phosphorylated dNTPs is expected to have lower overall yield relative to the first round of synthesis from the same batch of nucleotides.

Figure 4A:
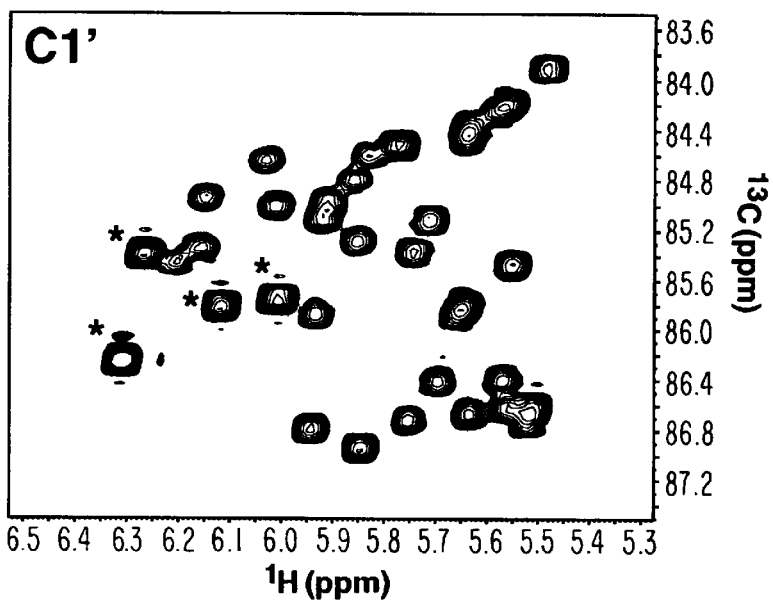
FIG. 4 depicts the sequence fidelity of DNA product 2 prepared by the method of the present invention in a single constant-time $^{13}C$—$^{1}H$ HSQC spectrum. The asterisks in each panel indicate crosspeaks of at least two proton intensity.
Figure 4B:
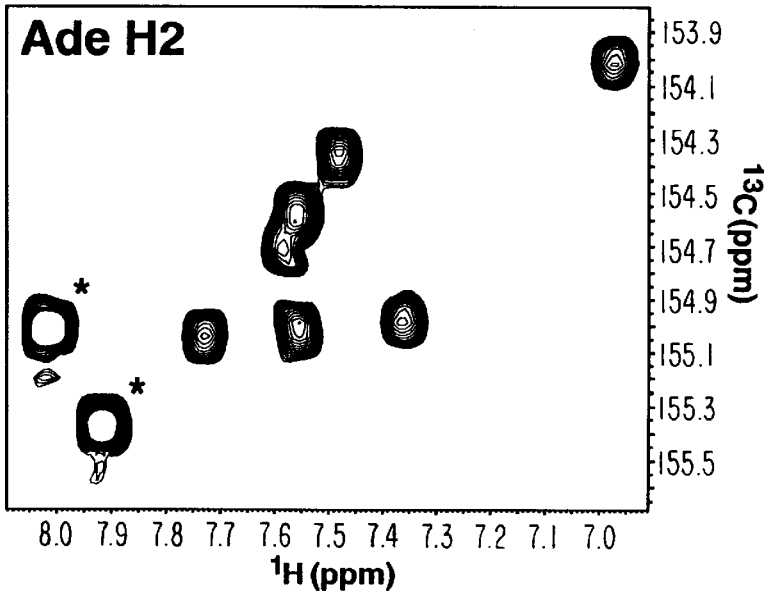
Figure 4C:
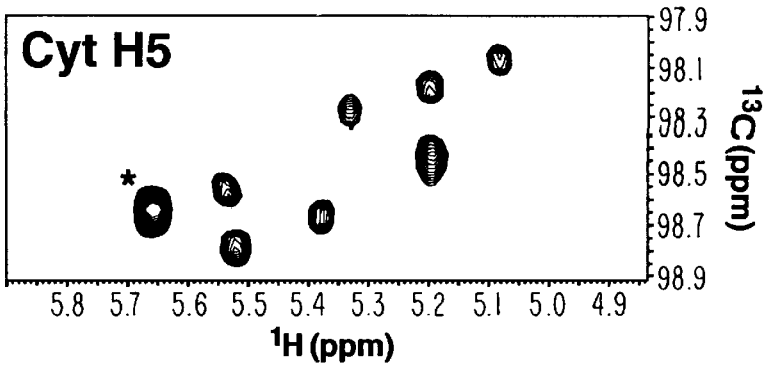

The method of the present invention produces a quantity of polynucleotide sequence of high sequence fidelity of DNA as compared with the input sequence. This is readily verified by a constant-time $^{13}C$—$^{1}H$ HSQC experiment and/or homonuclear NOESY. The simplest verification of DNA sequence is to count the number of $H_5$—$C_5$ crosspeaks of cytidine residues and $H_2$—$C_2$ crosspeaks of adenine residues present in the HSQC spectrum, as noted in the Examples below. If homonuclear NOESY is used, the cytidine $H_5$—$H_6$ crosspeaks and the thymine methyl groups can be identified and counted without sequence-specific assignment due to their unique chemical shifts. Since there is one $H_5$—$C_5$ (or $H_5$—$H_6$) crosspeak per GC basepair and one adenine $H_2$—$C_2$ crosspeak (or methyl crosspeak) per AT basepair, the composition of the product DNA is readily verified. For 2, eleven adenine $H_2$—$C_2$ correlations (two crosspeaks have two proton intensities) and nine cytidine $H_5$—$C_5$ correlations (one crosspeak has two proton intensity) are expected and observed (FIG. 4). An additional verification of the sequence can be accomplished by counting the number of $H_1$—$C_1$, crosspeaks of the sugars which should equal the total number of nucleotides in the sequence, although degeneracies in the $^{13}C_1$, shifts may preclude resolution of a full set. In the Examples herein, 37 of 40 crosspeaks are readily seen in the $^{13}C$—$^{1}H$ HSQC spectrum of SEQ ID NO:3/4 (4 crosspeaks have two proton intensities), nearly consistent with the expected number for a 20 basepair duplex; the remaining crosspeaks are assumed to be degenerate. Sequence-specific assignment of the $^{1}H$ resonances can be accomplished by a homonuclear NOESY experiment, but the resolution of $^{13}C$ chemical shifts may not be adequate to fully 5 assign their carbon shifts in a $^{13}C$—$^{1}H$ HSQC spectrum on the basis of the proton chemical shifts alone.

The preparation by the instant method of preselected polynucleotide sequences, in particular isotopically enriched sequences, of the quantity and quality as described above, numerous utilities of such sequences are noted, particularly as relate to the macromolecular interactions between a preselected polynucleotide sequences and another macromolecule, such as a protein or another polynucleotide sequence. Possible macromolecular interactions investigatable by the methods herein are not limiting and may include other polynucleotide sequences including DNA, RNA, duplex DNA, single-stranded DNA, triplex DNA, quadruplex DNA, 3-way junction DNA, and 4-way junction DNA, and another macromolecule including but not limited to peptides, proteins, DNA, RNA, duplex DNA, single-stranded DNA, triplex DNA, quadruplex DNA, 3-way junction DNA, 4-way junction DNA, and fragments thereof. The instant methods may be used for identifying a macromolecular binding site on a preselected polynucleotide sequence comprising the steps of:

a. preparing an isotopically enriched preselected polynucleotide sequence in accordance with the foregoing methods of preparing a quantity of a preselected polynucleotide sequence;

b. conducting NMR spectroscopy with a mixture of a preselected macromolecule and said preselected polynucleotide sequence;

c. detecting chemical shift perturbations between free and bound states at specific reporter atoms in said preselected polynucleotide sequence; and d. correlating said perturbations with the presence of a macromolecular binding site between said preselected macromolecule and said preselected polynucleotide sequence.

In another embodiment, a method for identifying agents capable of modulating the interaction between a preselected macromolecule and a preselected polynucleotide sequence is provided. The method comprises the steps of:

a. preparing an isotopically enriched preselected polynucleotide sequence in accordance with the foregoing methods of preparing a quantity of a preselected polynucleotide sequence;

b. conducting NMR spectroscopy with a mixture of the preselected macromolecule and said preselected polynucleotide sequence in the absence and presence of said agent;

c. detecting changes in chemical shifts between free and bound states at specific reporter atoms in said preselected polynucleotide sequence as a consequence of the presence of said agent; and d. correlating said changes with the modulating by said agent of said interaction between said preselected macromolecule and said preselected polynucleotide sequence.

The aforementioned method is useful for identifying not only agents which interfere with, or antagonize, the interaction between the preselected polynucleotide sequence and the macromolecule, but also those that may promote their association. In particular, the methods herein are useful in investigating the interaction between DNA and transcription factors and identifying means to modulate these interactions for therapeutic benefit.

The aforementioned methods employing heteronuclear NMR spectroscopy for the study of the interactions between DNA and macromolecules such as proteins, and the described utilities, may be better understood by reference to the Examples of the particular DNA sequences and protein investigated herein. The DNA-binding domain of the transcription factor PEBP2/CBF, termed the Runt-domain, binds to a conserved DNA sequence PyGPyGG where Py can be either cytidine or thymine (19, 20). The three-dimensional structure of the PEBP2/CBF Runt-domain bound to DNA indicates only 20 interfacial contacts with the DNA in a 27 kD complex (20). These contacts are deemed insufficient to unambiguously define the protein/DNA interface. The application of heteronuclear NMR to DNA in the utility of the instant application reveals important new information which further delineates the sites of protein/DNA interaction. A conventional $^{15}$N—$^1$H COSY spectrum demonstrates the excellent dispersion of protein and DNA chemical shifts possible in a single experiment, even at molecular weights in excess of 30 kD. The immediate benefit of simultaneous protein and DNA chemical shift resolution is apparent by consideration of the chemical shift changes observed for the imino-protons of the DNA in the context of a macromolecular complex. The nucleotide position(s) of likely protein/DNA interaction may be predicted, in part, from a qualitative analysis of chemical shift changes for the imino protons and nitrogens between free and bound DNA. This data indicates that the Runt-domain binds to DNA in the proximity of the three consecutive GC base pairs within the core binding sequence for the protein. This type of experiment can also form the basis of the identification of protein binding sites on DNA characteristic of a particular DNA sequence, which does not require any prior knowledge of the protein structure or optimal DNA-binding sequence and can be accomplished in an experiment taking only a few minutes.

In addition to the prediction of protein binding sites, heteronuclear NMR spectroscopy of DNA provides the opportunity to observe interfacial contacts with proteins that have previously been inaccessible to the NMR structural biologist. Important new information which becomes accessible with the advent of the method for the preparation of quantities of polynucleotide sequences of the present invention is the identification of hydrogen-bonded atoms of the DNA at a protein/DNA interface. The $N_4$-amino protons of cytidine are typically poorly resolved in conventional homonuclear $^1$H-NOESY of protein/DNA complexes due to their overlap with the chemical shifts amide and aromatic ring protons of the protein. Thus, it has previously been difficult to analyze the NOE spectrum of the amino and imino protons of the DNA in the absence of a pre-existing model for the protein/DNA interaction. NMR utilizing isotopically enriched polynucleotide sequences prepared by the method of the present invention resolves this ambiguity in a single $^{15}$N-edited NOE experiment due to the complete resolution of protein and DNA $^1$H and $^{15}$N chemical shifts for each species in the complex. As shown in the Examples below, the resolution of the cytidine amino protons realized from the product prepared by the method of the instant invention permits the first observation of hydrogen-bonding at a protein/DNA interface in solution.

In unbound B-form DNA, one amino proton of cytidine is hydrogen-bonded in a GC basepair and resonates at 7.5 to 8.5 ppm. The second, non-hydrogen bonded proton is usually found at 6–7 ppm and is exchange-broadened due to hydrogen exchange with the bulk solvent. In the Runt-domain/DNA complex, the two cytidine amino-protons of basepair 14 are both found downfield, at 8.15 and 8.7 ppm respectively. These downfield resonances can be unambiguously assigned to the amino-protons of cytidine by observation of imino-to-amino NOEs at the $^{15}$N-chemical shift of cytidine $N_4$ and the corresponding observation of these NOEs at the $^{15}$N-chemical shift of guanine $N_1$ in the same basepair. Two observations permit the identification of the non-basepaired proton as the one which shifts downfield in the complex. Comparison of the NOE spectra of free and protein-bound DNA can identify which proton is shifted, but perturbation of the chemical shifts in the complex may leave some ambiguity in the assignment. An alternative is to ascertain this information directly from the $^{15}$N-edited NOESY spectrum of the complex. The amino-to-$H_5$ NOE for the non-basepaired proton would be expected to be significantly stronger than the NOE to the basepaired proton due to its closer distance to $H_5$ of the pyrimidine ring (~2.4 Å non-basepaired, ~3.7 Å basepaired assuming B-helix). Comparison of the intensity of the amino-to-H5 crosspeaks for basepair 14 indicates that the proton at 8.15 ppm must be the shifted proton in the complex; its amino-to-H5 crosspeak intensity is substantially greater than that to the amino proton at 8.7 ppm. The amino proton at 8.15 ppm also displays the weaker NOE to the imino proton of the basepair, consistent with its greater distance from the guanine $H_1$. Comparison of the cytidine amino proton chemical shifts of basepair 15 to those of basepair 14 illustrates the benefit of heteronuclear NMR to interfacial NOE analysis. For basepair 15, the two amino-to-imino NOEs are observed at the expected locations, 6.7 and 8.1 ppm, which correspond to the non-basepaired and basepaired amino protons, respectively. Thus, the application of the method of the instant application to DNA NMR permits residue-specific analysis of interfacial contacts even in a 33 kD protein/DNA complex.

The application of heteronuclear NMR methods to deoxyribonucleic acids provides the opportunity to overcome the limitations of homonuclear NMR to the study of DNA structure in solution. DNA structural analysis by NMR has been historically limited by the poor proton density of DNA, which precludes the direct measurement of long-range order from NOEs alone. The narrow $^1$H chemical shift dispersion of DNA further restricts structural analysis of dihedral angles from scalar coupling constants. Heteronuclear, multidimensional NMR can circumvent many of these limitations, enabling the opportunity to measure scalar coupling constants by quantitative J correlation (22), direct measurement of the sugar puckers from cross-correlated relaxation (18), basepair hydrogen bond strengths (19–20) and the identification of interfacial hydrogen bonding between protein and DNA, as described herein.

Two unexpected outcomes have been realized from the application of the methods of the present invention to complex biological systems. In the first instance, $^{15}$N-edited NMR of DNA establishes a type of footprint experiment for protein/DNA interactions with base resolution, equivalent to that of more cumbersome and time consuming chemical footprinting techniques. The 'NMR footprinting' experiment relies on the observation of chemical shift perturbations between free and bound states at specific reporter atoms of the DNA. The high sensitivity of a heteronuclear COSY experiment enables the application of this technology to relatively dilute solutions, perhaps no more than 100 mM, with experiment times that are only a few hours. The extension of this approach to perturbation measurements of purine N3 and N7 chemical shifts as well as to C5' at the phosphodiester backbone could provide a complete identification of contacts sites on the DNA for a sequence-specific binding protein without any prior knowledge of protein structure. Second, the application of the method of the present invention to the study of protein/DNA complexes has revealed the first observation of hydrogen-bonding at a protein/DNA interface in solution. Extension of the recently described measurement of cross-hydrogen bond scalar couplings to interfacial hydrogen bonds may allow for the direct, quantitative analysis of DNA recognition mechanisms by proteins in solution (23–24).

The fact that the present method can produce a large quantity of DNA that is inherently single-length may also be advantageous for other biophysical studies, most importantly for X-ray crystallography. Overhang or blunt-ended DNA can be prepared by the present methods with the introduction of the appropriate restriction endonuclease cleavage site, offering a wide variety of DNA ends to promote crystallization.

A further use of the methods herein is in the preparation of antisense oligonucleotides. Antisense nucleic acids are DNA or RNA molecules that are complementary to at least a portion of a specific mRNA molecule. In the cell, they hybridize to that mRNA, forming a double stranded molecule. The cell does not translate an mRNA in this double-stranded form. Therefore, antisense nucleic acids interfere with the expression of mRNA into protein.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Preparation of Quantities of a Preselected Polynucleotide Sequence

Natural abundance nucleotides were purchased as calibration standards from Amresco. RNase-free DNaseI was from Worthington, Nuclease P1 from Boehringer-Mannheim, EcoRV endonuclease from Promega; myokinase (MK), pyruvate kinase (PK), guanylate kinase (GK) and nucleoside monophosphate kinase (NMPK) were purchased from Sigma. The starting DNA templates (see Table I) were synthesized on an Applied Biosystems 394 DNA synthesizer using standard phosphoramidite chemistry and purified by reversed-phase HPLC followed by preparative 20% denaturing PAGE. The method of the present invention was performed on a Stratagene Robocycler Gradient 40 thermal cycler. Recombinant Pfu DNA polymerase was expressed and purified from a clone purchased from the ATCC (accession number 87496; ref. 25). Recombinant yeast thymidylate monophosphate kinase (TMPK) was expressed and purified as a GST-fusion protein. E. coli cytidylate monophosphate kinase (CMPK) was expressed and purified. $^{15}NH_4Cl$ and $^{13}C$-glucose were purchased from Isotech.

Genomic DNA of Escherichia coli, strain BL21 or HMS174, was isolated in three ways. Bacteria were grown on defined media with $^{15}NH_4Cl$ and/or $^{13}C$-glucose as the sole nitrogen and carbon sources. For the isolation of only isotopically-enriched genomic DNA, cells were lysed in a 10 mM Tris, 10 mM EDTA, 100 mM NaCl, pH 8.0 buffer using a french press in lieu of SDS. The lysate was extracted with phenol/chloroform to isolate the DNA (6). For the simultaneous isolation of isotopically-enriched $His_6$-tagged proteins and DNA, cells were lysed in a 50 mM Tris, 1.0 M NaCl, 30 mM imidazole, 10 mM benzamidine hydrochloride, pH 8.0 by French press. The lysate was clarified by centrifugation and fractionated with metal-chelate chromatography using standard procedures. The column flowthrough was subsequently phenol/chloroform extracted to isolate the DNA (6). For the simultaneous isolation of soluble, untagged proteins and DNA, cells were lysed in a 20 mM Tris, 10 mM $Na_2EDTA$, 1.0 M NaCl, 10 mM DTT, 10 mM benzamidine hydrochloride, pH 8.0. The lysate was clarified by centrifugation and the bulk proteins precipitated by the addition of ammonium sulfate to 70% saturation. The protein of interest can be recovered from the ammonium sulfate pellet by dialysis and FPLC chromatography. The supernatant following ammonium sulfate precipitation was twice dialyzed against four liters of 10 mM Tris, 100 mM NaCl, pH 8.0 buffer at 4° C. prior to phenol/chloroform extraction. Isolated nucleic acids were digested and purified according to published procedures (6, 12–13, 27). 6.6 mmoles of $^{13}C$ and/or $^{15}N$ uniformly-enriched dNMPs were typically recovered from each gram of wet cell paste.

Enzymatic phosphorylation of dNMPs was achieved in a single step by a modification of established procedures, to include the utilization of recombinant TMPK and CMPK to phosphorylate dTMP and dCMP, respectively (12–13, 28). Special care must be taken to appropriately adjust the ratio of $[dNTP]:[Mg^{2+}]$ to be no more than about 1:2. The product mixture is ultrafiltered with Centricon-3 (Amicon) to remove protein and stored at 4° C. The concentration of individual dNMPs and dNTPs in a mixture were determined by quantitative RP-HPLC using calibration standards. The error in nucleotide concentration was typically found to be ±10% using this procedure. Simple measurement of absorbance of a nucleotide mixture was found to be unreliable, severely reducing overall yield.

DNA synthesis was carried out in 40×500 μg reaction vials in a Stratagene Robocycler 40 with the gradient option and 'hot top'. Peltier-driven thermal cyclers were found to be less efficient for carrying out the instant method. For each desired sequence, the annealing temperature in both synthetic steps was optimized with the gradient feature over a 16° C. range in 2° C. increments by examining the amount of restricted product DNA in 0.7% agarose gel electrophoresis. The results are shown in Table 2, below.

TABLE 2

| | Optimal annealing temperatures | |
|---|---|---|
| DNA Template | Step 1 ($T_1$ ° C.) | Step 2 ($T_1$ ° C.) |
| SEQ ID NO: 1/2 | 49 | 60 |
| SEQ ID NO: 5/6 | 51 | 66 |
| SEQ ID NO: 9/10 | 43 | 64 |

A typical Step 1 reaction contained: 0.1 μM each of gel purified template, 2 mM dNTP mixture, 4 mM $MgSO_4$, 1× Pfu reaction buffer (20 mM Tris, 10 mM KCl, 10 mM $(NH_4)_2SO_4$ 0.1% Triton-X-100, pH 8.8 with 0.12 mg/mL BSA) and 3.25 μg recombinant Pfu DNA polymerase. The reaction mixture was heated to 95° C. for 5 minutes followed by 25 cycles of 95° C. for 45 s, $T_1$° C. for 2 min, and 72° C. for 4 min. A final incubation at 72° C. for 10 min was followed by cooling at 4° C. to quench polymerization. A typical Step 2 reaction contained: 50 μL Pool A, 2 mM dNTPs, 4 mM $MgSO_4$, 1× Pfu reaction buffer, 3.25 μg recombinant Pfu DNA polymerase. Single repeat DNA (ca. 35 pmol) derived from restriction of a separate run or by restriction of the original templates may also be added at this stage to enhance overall product yield by as much as 20%. Cycling of Step 2 was 95° C. for 5 minutes followed by 60 cycles of 95° C. for 45 s, $T_2$° C. for 2 min, and 78° C. for 4 min. Thermal cycling was followed by incubation at 78° C. for 10 min and cooling at 4° C. to stop the reaction.

200 units of EcoRV endonuclease was added/500 μL Step 2 reaction in the same vessel. Dithiothreitol (DTT) was added to 1 mM final concentration; $MgCl_2$ to 1.4 mM; and NaCl to 125 mM. The enzyme was carefully mixed by gentle inversion of the reaction tube. The mixture was incubated at 37° C. for 10 hours. The course of digestion was monitored by 1.5% agarose gel electrophoresis.

Digested Step 2 reactions were pooled, 0.2 micron filtered and purified by DEAE ion-exchange HPLC using a preparative Vydac 301 VHP column (25×100 mm). The column was equilibrated with 25 mM sodium phosphate, pH 7.4, 90 mM NaCl. The digested product DNA was injected (5 ml aliquots) and washed over the column for three column volumes to remove the unincorporated dNTPs and other reaction components. Product DNA was eluted using a gradient of 90 mM to 360 mM NaCl over 15 minutes at a flow rate of 10 ml/min. Fractions containing the main DNA peak were collected and dialyzed against 1 mM sodium phosphate (pH 7.0) and concentrated by lyophilization. The yield of product DNA was determined by measuring the absorbance at 260 nm using an extinction coefficient of 50 $\mu$g/ml/$A_{260}$ unit. The pool of unincorporated nucleotides was desalted on a preparative C18 RP-HPLC column (Dynamax), converted to the sodium form and phosphorylated as above for future use (6, 12–13, 23).

All NMR spectroscopy was conducted with either a Bruker DMX500 or DMX600 equipped with a triple resonance, actively shielded proton detect probe with single-axis z-gradients operating at 38° C. Sample concentrations were 1 mM throughout. $^{13}C$—$^1H$ constant-time HSQC was performed as described with $^1J_{cc}$ tuned to 40 Hz for sugars and 68 Hz for bases with the $^{13}C$ carrier placed at 85 or 140 ppm, respectively(29). Acquisition times were 14.2 ms ($t_1$) and 21.2 ms ($t_2$) with spectral widths of 55 ppm ($t_1$) and 10 ppm ($t_2$), 4 scans per increment. $^{13}C$ decoupling during $t_2$ was accomplished with GARP at 4.4 kHz (30). $^{15}N$—$^1H$ HSQC spectra were collected as described with acquisition times of 26.3 ms ($t_1$) and 57 ms ($t_2$) employing GARP (30) decoupling during $t_2$ at 1.2 kHz and water flip-back pulses with the $^{15}N$ carrier frequency placed at 119.0 ppm (31). Spectral widths were 42 ppm ($t_1$) and 20.8 ppm ($t_2$), 8 scans per increment. $^{13}C$-edited NOESY-HMQC was performed as described with acquisition times of 8.8 ms ($t_1$), 2.3 ms ($t_2$) and 30.5 ms ($t_3$) with 4.4 kHz GARP (30) decoupling during $t_3$ and the $^{13}C$ carrier placed at 85 ppm (32). Spectral widths were 9.1 ppm ($t_1$), 40 ppm ($t_2$) and 14 ppm ($t_3$), 8 scans per increment. $^{15}N$-edited NOESY-HSQC was performed with acquisition times of 5.2 ms ($t_1$), 5.1 ms ($t_2$) and 41 ms ($t_3$), water flip-back pulses and a 1.2 kHz GARP (30) decoupling field during $t_3$ with the $^{15}$—N carrier placed at 119.0 ppm. $^{31}$ Spectral widths were 20.3 ppm ($t_1$), 40 ppm ($t_2$) and 20.8 ppm ($t_3$), 16 scans per increment. In all cases, quadrature detection in the indirect dimensions was achieved using States-TPPI.[33] Data were processed with nmrPipe (34) and analyzed with PIPP (35).

Figure 1B:
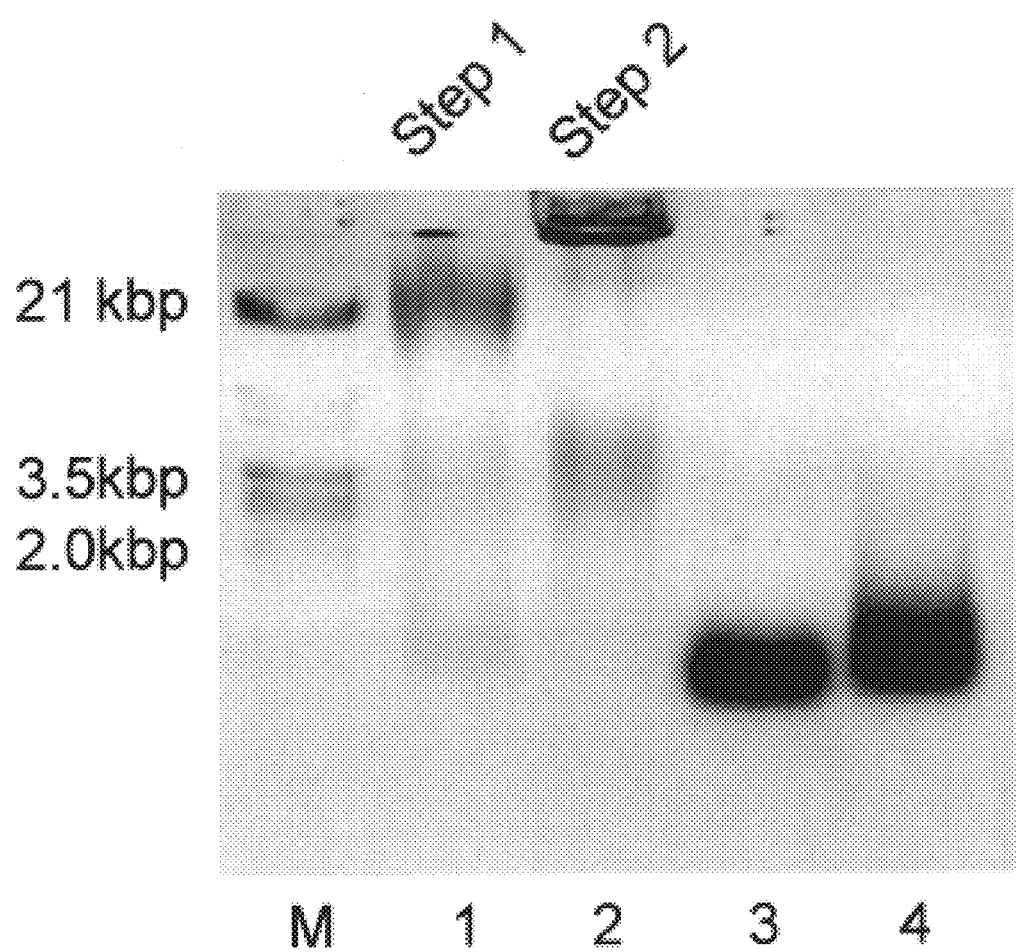
FIG. 1B shows the course of synthesis of a preselected polynucleotide sequence using 0.7% agarose gel electrophoresis. Lane M comprises molecular weight markers. Lane 1 shows the product of Pool A from FIG. 1A. Lane 2 shows the product of Step 2 of FIG. 1A before endonuclease cleavage. Lane 3 shows the product of the endonuclease cleavage of the product of Step 2. Lane 4 shows the increased product yield resulting from the addition of preselected polynucleotide sequence monomer at the beginning of Step 2.

As shown in FIG. 1A, the method of the present invention requires two steps, the first of which prepares a self-priming/self-propagating template pool and the second which synthesizes long, tandemly-repeated DNA. The course of synthesis is followed by 0.7% agarose gel electrophoresis (FIG. 1B). In step a), a tandem repeat of the desired sequence is added to the reaction mixture as a blunt-ended duplex. b) Thermal cycling converts the blunt-ended duplex into a self-priming repeat, creating a pool of different length DNAs 2–20 kilobasepairs in length (FIG. 1B: Pool A, lane 1). c) Pool A is diluted 10-fold in Step 2 into a series of reactions which create long tandem repeats. At the beginning of Step 2, optional addition of primer of monomer duplex DNA containing a single repeat of the desired sequence can be added to increase the overall yield. It is imagined that both linear and branched DNAs might be formed during amplification. Extensive thermal cycling (FIG. 1A, step d; FIG. 1B, lane 2) followed by restriction with EcoRV (FIG. 1A, step e; FIG. 1B, lane 3) results in milligram quantities of single-length DNA product of the desired sequence. The enhanced product yield resulting from the addition of single repeat DNA at point c) can be appreciated by comparison of lanes 3 and 4 of FIG. 1B.

Figure 2A:
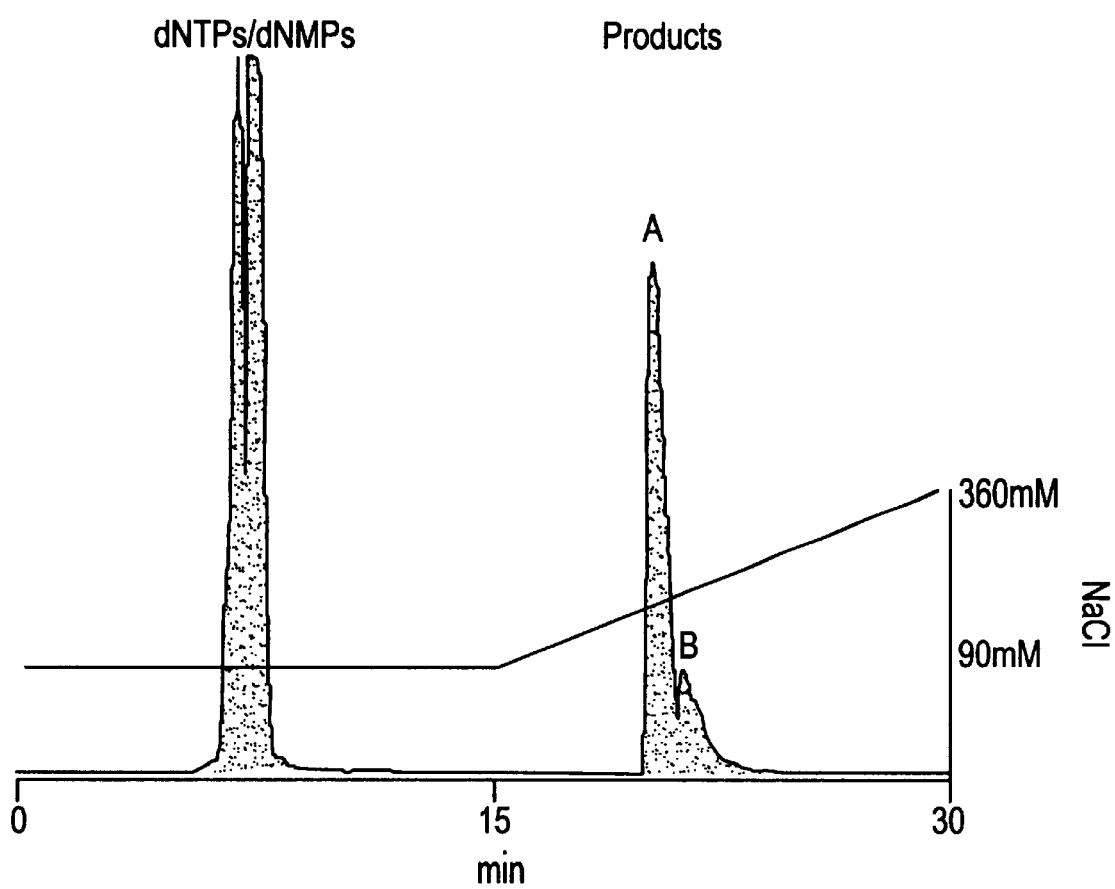
FIGS. 2A and 2B depict the purification of products prepared in accordance with the present invention. The endonuclease cleaved product DNA can be purified in a single step by DEAE ion-exchange HPLC (FIG. 2A). Denaturing polyacrylamide gel electrophoresis demonstrates that the two strands of the product DNA are resolved (FIG. 2B, lanes 1 and 2). HPLC peaks A and B are shown in lanes 3 and 4, respectively. Product B from FIG. 2A is typically no more than 10% of the total DNA produced (lane 4).
Figure 2B:
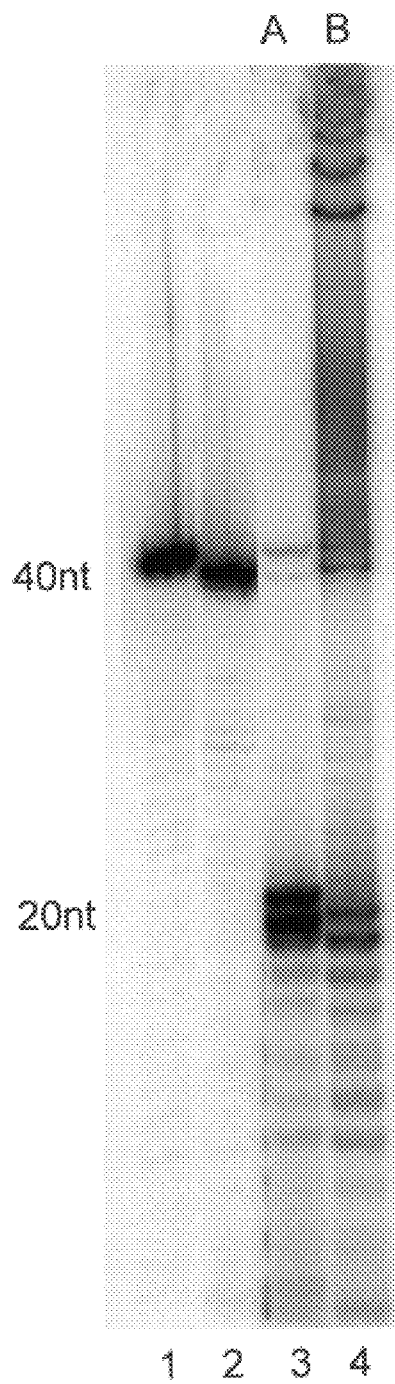

The endonuclease-cleaved (restricted) product DNA was purified in a single step by DEAE ion-exchange HPLC in 25 mM sodium phosphate employing a biphasic gradient. Isocratic elution at 90 mM NaCl to recover unreacted dNTPs/dNMPs is followed by a linear gradient over 15 minutes from 90–360 mM NaCl to elute the product DNA. The products separate into two fractions (FIG. 2A). The main product (FIG. 2A, peak A) is single length DNA of desired sequence (FIG. 2B, lane 3). Denaturing polyacrylamide gel electrophoresis demonstrates that the two strands of the product DNA are resolved in 20% gels (FIG. 2B, lanes 1 and 2) and form essentially the sole product seen in fraction A. The small quantity of 'failed' product (FIG. 2A, peak B; FIG. 2B, lane 4) is comprised of unrestricted DNA fragments as well as a some smaller DNAs resulting from non-specific cleavage by EcoRV under these reaction conditions. Product B is typically no more than 10% of the total DNA produced.

The amount of peak B product, if any, may be reduced by adjusting the conditions during the digestion step described above. Judicious choice of cleavage conditions, such as by way of non-limiting example, adjusting the concentration of DTT, NaCl and/or $MgCl_2$, will reduce or preclude peak B from forming. The skilled artisan will readily be able to increase the yield of desired product and reduce the level of "failed" product.

Figure 3A:
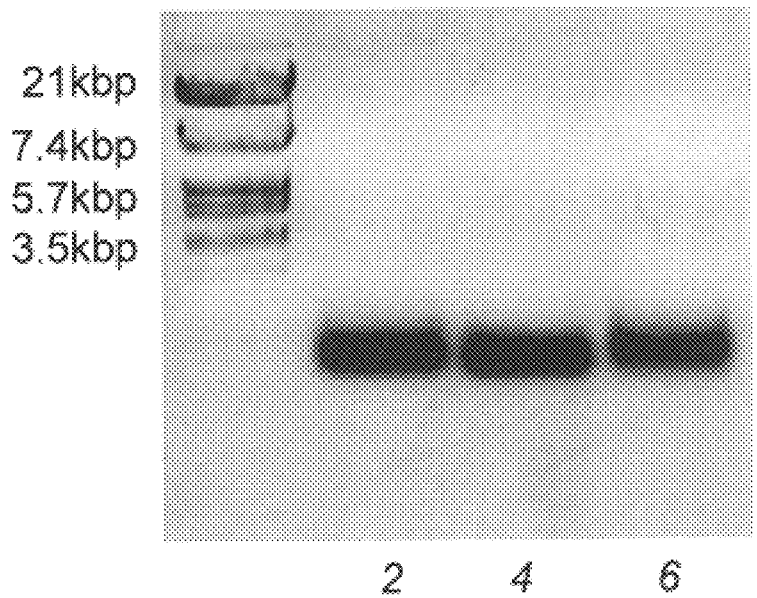
FIGS. 3A and 3B depict the products of the method of the present invention on templates 2, 4 and 6 of Table 1 after endonuclease digestion and visualization by ethidium bromide staining of a 0.7% agarose gel (FIG. 3A). Products 2, 4 and 6 were analyzed by 15% native PAGE following DEAE ion-exchange chromatography and $^{32}P$ end-labeling with T4 polynucleotide kinase.
Figure 3B:
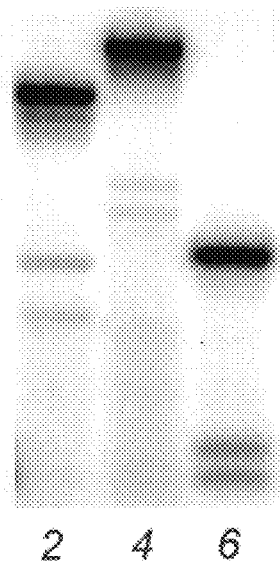

The synthesis described herein is independent of either sequence or length of target DNA. 500 ml reactions employing templates which produced products SEQ ID NO:3/4, SEQ ID NO:7/8 and SEQ ID NO:11/12 were digested with EcoRV and visualized by ethidium bromide staining of a 0.7% agarose gel. The band intensities are nearly equal for the different length products indicating no length dependence to the product yield in the instant method (FIG. 3A). Products SEQ ID NO:3/4, SEQ ID NO:7/8 and SEQ ID NO:11/12 were analyzed by 15% native PAGE following DEAE ion-exchange chromatography and $^{32}p$ end-labeling with T4 polynucleotide kinase. The gel of FIG. 3B indicates that the duplex products are single length. The trace amount of DNA seen as a doublet in each lane is a small amount of denatured duplex formed during electrophoresis.

EXAMPLE 2

Fidelity of the Product

FIG. 4 depicts the sequence fidelity of DNA products prepared as described above. The sequence fidelity of product SEQ ID NO:3/4 was assessed in a single constant-time $^{13}C$—$^1H$ HSQC spectrum. This sequence contains nine G.C and eleven A.T basepairs (see Table 1) which can be verified by counting the number of cytidine —$H_5$ and adenine $C_2$—$H_2$ crosspeaks. The total number of nucleotides in the product DNA can also be counted from the $C_1$—H, crosspeaks, although the degeneracy of $^{13}C$ chemical shifts may preclude resolution of a full set, depending on sequence composition and length. Thirty-seven of the expected 40 $C_1$—$H_1$, crosspeaks may be counted in the spectrum of product SEQ ID NO:3/4 assuming four crosspeaks have at least two proton intensity. The asterisks in each panel indicate crosspeaks of at least two proton intensity.

Figure 5A:
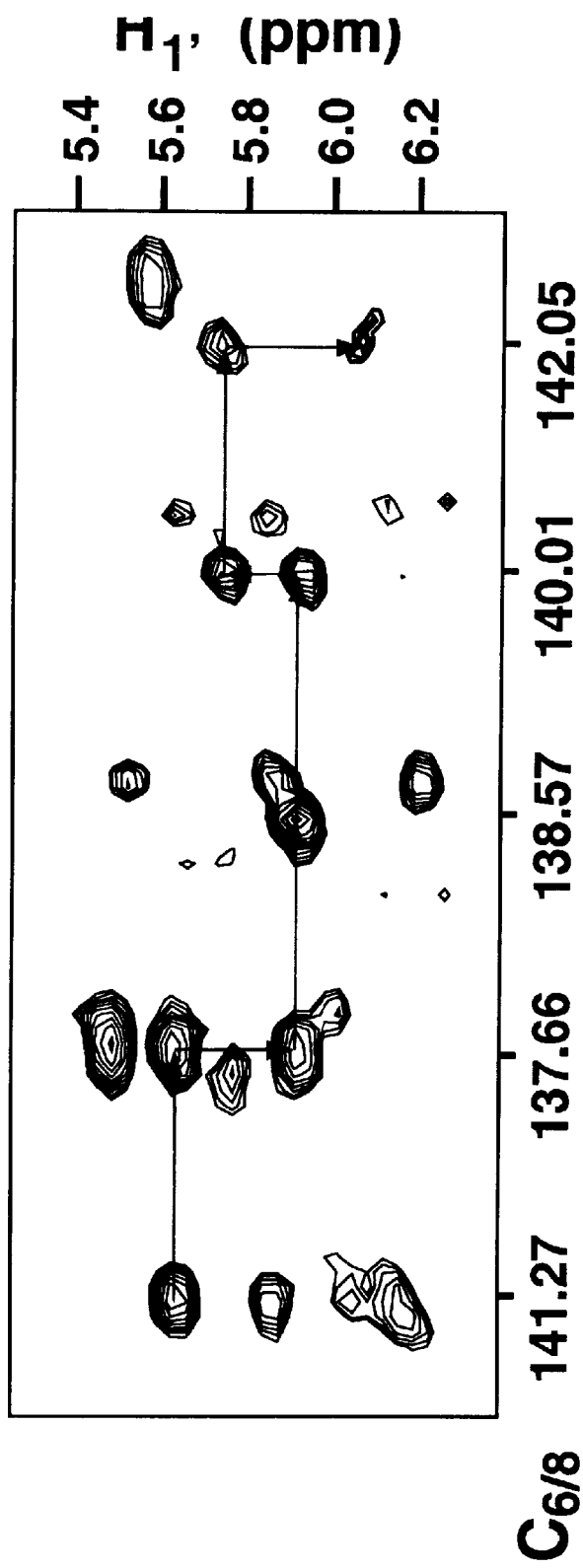
FIG. 5 shows the sequential assignment of uniformly $^{13}C/^{15}N$-enriched DNA of product 2 using a $^{13}C$-edited NOESY spectrum (120 ms mixing time) to simultaneously assign $^{1}H$ and $^{13}C$ chemical shifts of isotopically-enriched DNA in $D_2O$. Shown is a small segment of one strand of product 2. The sequential assignment can be followed through the strips at either the $^{13}C$ chemical shift of the bases ($C_{6/8}$, top panel) or $C_1$, (bottom panel).
Figure 5B:
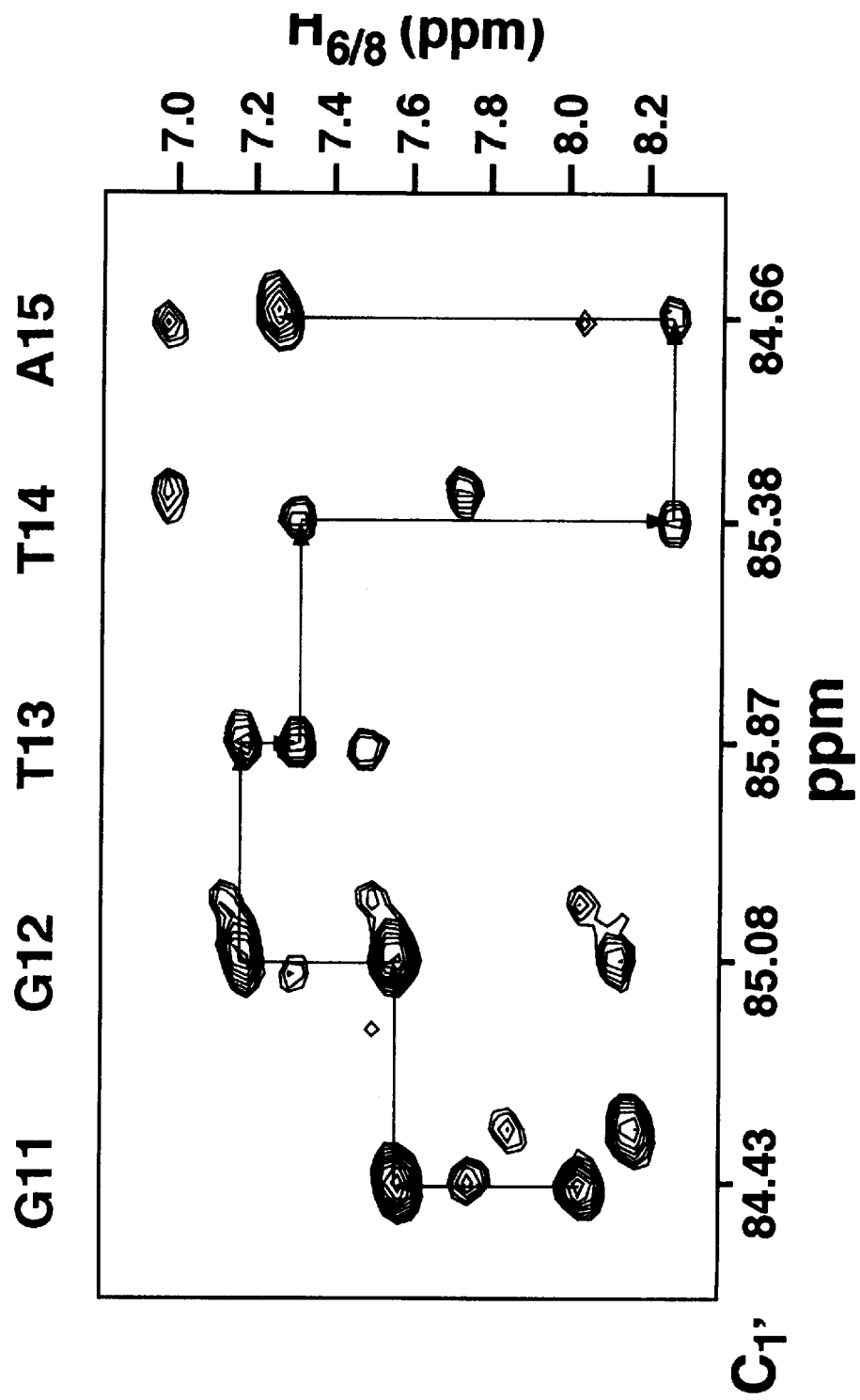

The symmetry of a $^{13}C$-edited NOESY spectrum (120 ms mixing time) can be utilized to simultaneously assign $^1H$ and $^{13}C$ chemical shifts of isotopically-enriched DNA in $D_2O$. Shown in FIG. 5 is a small segment of one strand of product SEQ ID NO:3/4. The sequential assignment can be followed through the strips at either the $^{13}C$ chemical shift of the bases ($C_{6/8}$, top panel) or $C_1$, (bottom panel). The assignment begins from $C_8/H_8$ strip at the intraresidue NOE to $H_1$, of residue 11 and can be followed along $H_1$, to the next base $C_8/H_8$ strip at residue 12. The intraresidue crosspeak to $H_1$, of residue 12 is then the starting point for walking along the sequence to the next base at position 13. The identical path can be followed beginning at the $C_1/H_1$, strip of residue 11 at the intraresidue crosspeak to its own $H_8$. The redundancy of the sequential connectivity path between atoms in each subspectrum permits the resolution of crosspeaks in one subspectrum that may not be resolved in its complement. Residue 13 in the sequence has a degenerate $H_1$, chemical shift with that of residue 12 when viewed in the $C_{6/8}$ subspectrum. The degeneracy is broken in the $C_1$, subspectrum where the $H_8$ proton of residue 12 is resolved from the $H_6$ proton of residue 13.

EXAMPLE III

Investigation of Polynucleotide-Protein Interactions

Figure 6:
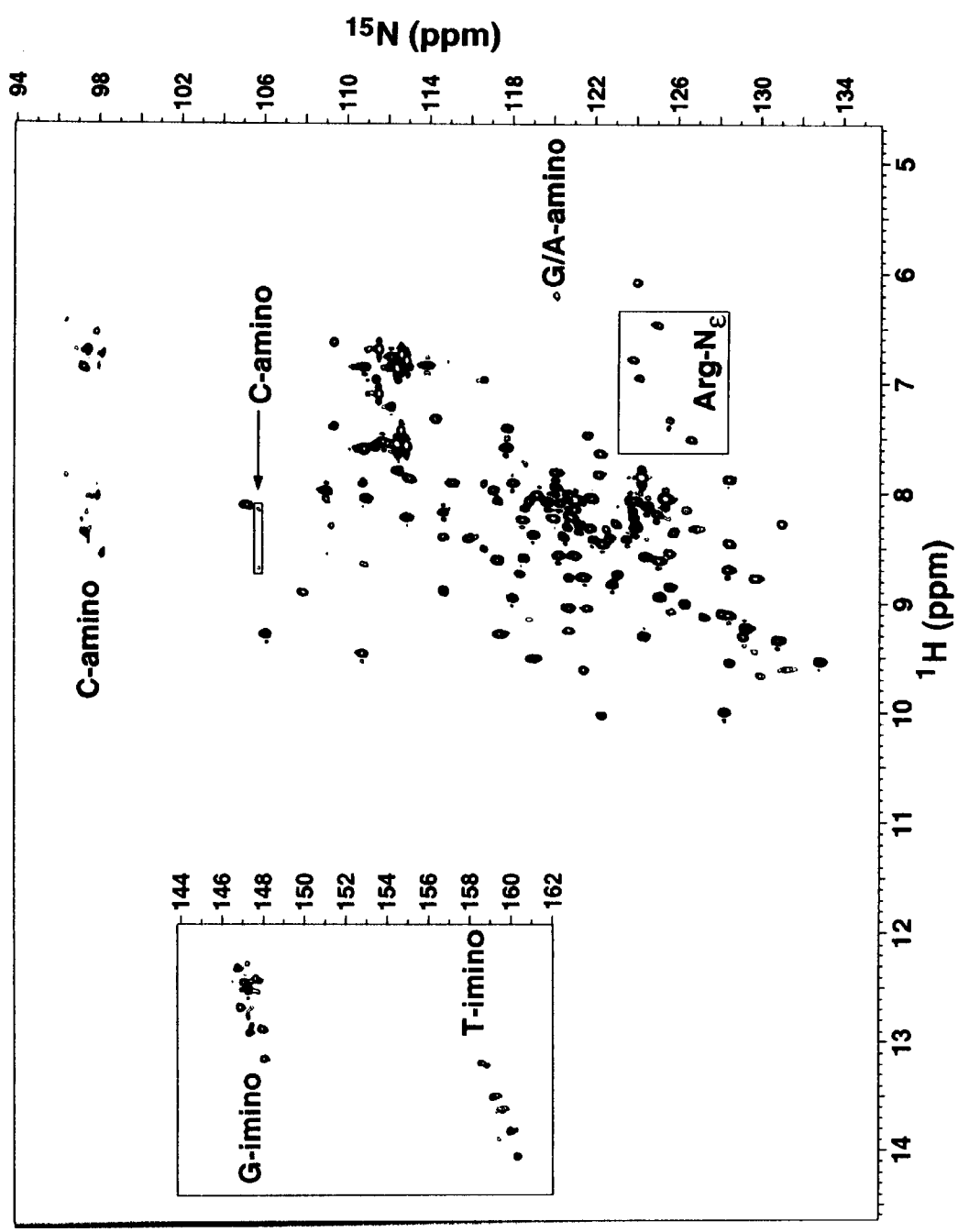
FIG. 6 depicts the distribution of $^{15}$N and $^{1}$H chemical shifts in the 33 kD Runt-domaine/DNA complex. Uniformly $^{15}$N-enriched Runt-domain and product 4 were utilized to form a protein/DNA complex. The box on the lower right indicates the sidechain $N_e$—$H_e$ crosspeaks of arginines.

Uniformly $^{15}$N-enriched Runt-domain and product SEQ ID NO:7/8 were utilized to form a protein/DNA complex as previously described (20). The spectrum in FIG. 6 illustrates the exceptional chemical shift resolution and sensitivity of both protein and DNA resonances even at this large molecular weight. Imino protons of the DNA are folded into the spectrum and have opposite phase to signals from the protein, but have not been discriminated in this representation. The box on the lower right indicates the sidechain $N_e$—$H_e$ crosspeaks of arginines. Comparison of these spectra to those of unlabeled DNA of the same sequence indicates two significant features. First, one cytidine amino group is shifted downfield to $^{15}$N=105.66 ppm in the complex. Second, a single purine amino-proton/nitrogen correlation can be seen folded in at $^{15}$N=120 ppm, the first observation of a purine amino proton in a protein/DNA complex.

Figure 7A:
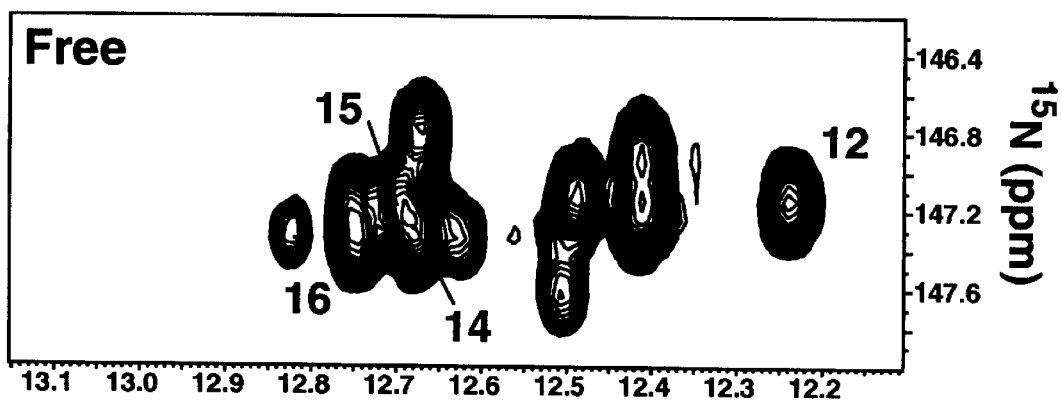
FIG. 7 depicts the core binding sequence of the Runt-domain is PyGPyGG where Py=cytidine or thymine. Selective chemical shift changes of the imino $^{1}$H and $^{15}$N chemical shifts for basepairs 14–16 and relatively little change at position 12 are shown.
Figure 7B:
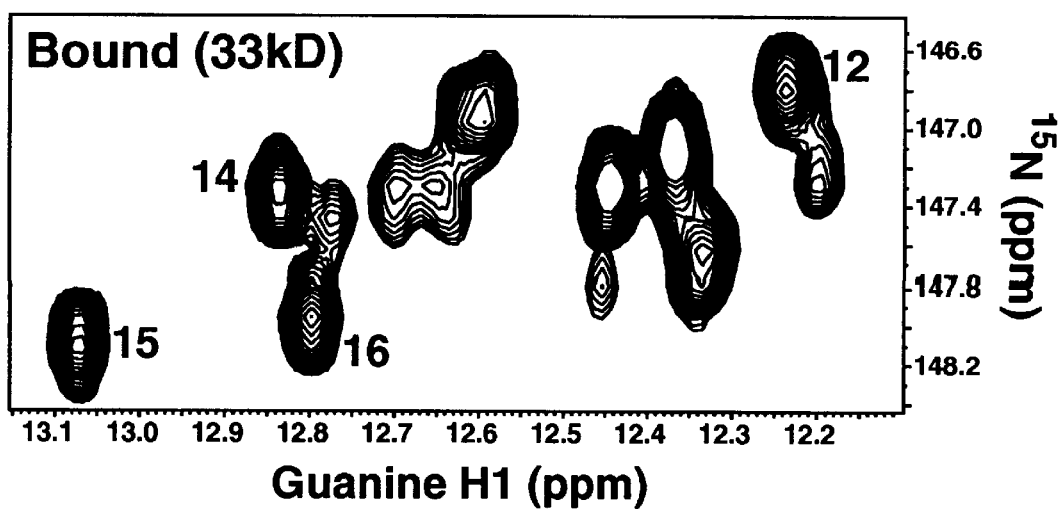

The core binding sequence of the Runt-domain is PyG-PyGG where Py=cytidine or thymine. Simple inspection of the guanine imino protons of free and protein-bound $^{15}$N-enriched DNA illustrates that there are selective chemical shift changes of the imino $^1$H and $^{15}$N chemical shifts for basepairs 14–16 and relatively little change at position 12 (FIG. 7). This data is consistent with the observation of base-specific NOEs between protein and DNA which are seen only at basepairs 14 and 15 in the complex. The remaining guanine imino protons lie outside of the core binding sequence for the Runt-domain and are relatively unperturbed by the presence of the protein.

Figure 8:
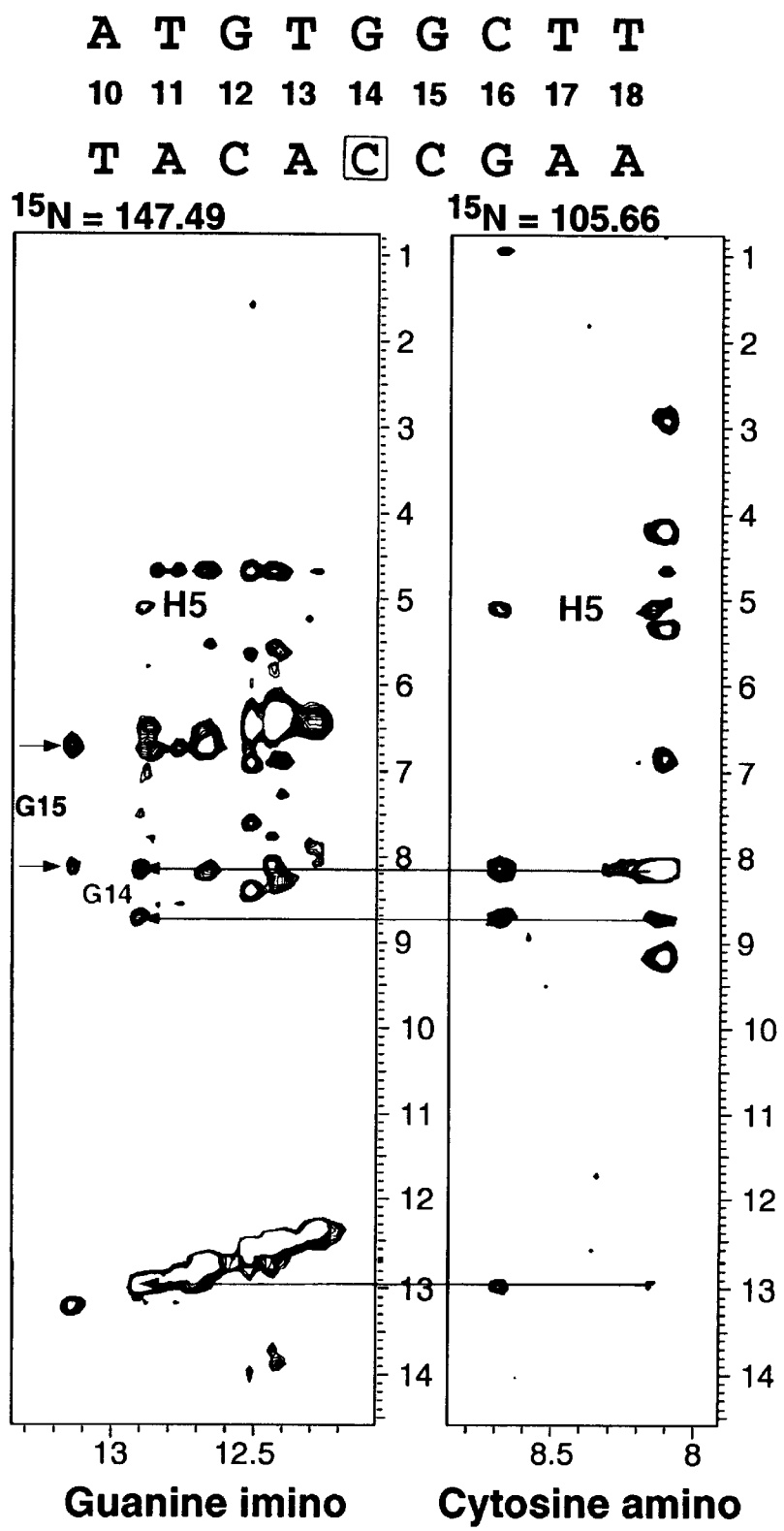
FIG. 8 depicts the interfacial hydrogen-bonding at the Runt-domain/DNA4 interface using $^{15}$N-edited NOESY (125 ms mixing time) of the Runt-domain/DNA complex.

$^{15}$N-edited NOESY (125 ms mixing time) of the Runt-domain/DNA complex confirmed that the pair of signals at $^{15}$N=105.66 ppm were cytidine amino protons of the DNA (FIG. 8). The protons at 8.15 ppm and 8.7 ppm at $^{15}$N=105.66 ppm display the expected crosspeaks to the imino proton of the same basepair. Both amino protons appear shifted down field, in contrast to those of all other cytidines of the DNA in the complex. The downfield shift to 8.15 ppm of the non-basepaired cytidine amino proton is diagnostic for hydrogen-bonding which can only have the protein domain as a partner. Although comparison to the NOESY spectrum of the free DNA can confirm which of the two amino protons is shifted downfield, it may also be determined by examination of the NOE intensities in the complex spectrum. The non-basepaired amino proton should display a stronger NOE to the $H_5$ of the pyrimidine ring and a weaker NOE to the imino proton of the guanine partner. This pattern is seen for the amino proton at 8.15 ppm. Comparison of the peak pattern of G14 to the amino-to-imino crosspeak pattern of G15 illustrates that evidence for interfacial hydrogen-bonding to DNA bases at a protein/DNA interface can be resolved in complexes as large as 33 kD.

EXAMPLE IV

Identifying Modulators of Polynucleotide-Protein Interactions

Chemical shift perturbation analysis can also be used to identify compounds which can disrupt a specific protein/DNA interaction. This can be achieved by titration of small molecule into a solution of the protein-bound DNA and watching for the change of monitored chemical shifts back to those of the free DNA in solution, as described in the Examples herein. In this manner, specific molecules which can disrupt DNA interactions with a protein can be specifically identified.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

References

1. Wüthrich, K. *NMR of Proteins and Nucleic Acids*; John Wiley & Sons: New York, N.Y.; 1986.
2. a) Clore, G. M.; Gronenborn, A. M. *Annu. Rev. Biophys. Biophys. Chem.* 1991, 20, 29–63. b) Clore, G. M.; Gronenborn, A. M. *Science* 1991, 252, 1390–99.
3. Bax, A.; Grzesiek, S. *Acc. Chem. Res*, 1993, 26,131–38.
4. Wagner, G. *Nature Struct. Biol.* 1997, 4 (supl.), 841–44.
5. Fesik, S. W.; Zuiderweg, E. R. P. Q. *Rev. Biophys.* 1990, 23, 97–131.
6. a) Batey, R. T.; Inada, M.; Kujawinski, E.; Puglisi, J. D.; Williamson, J. R. *Nucleic Acids Res.* 1992, 20, 4515–23. b) Batey, R. T.; Battiste, J. L.; Williamson, J. R. *Methods Enzymol.* 1995, 261, 300–322.
7. a) Nikonowicz, E. P.; Sirr, A.; Legault, P.; Jucker, F. M.; Baer, L. M.; Pardi, A. *Nucleic Acids Res.* 1992, 20, 4507–13. b) Pardi, A. Methods Enzymol. 1995, 261, 350–380.
8. a) Varani, G.; Tinoco, I. Q. *Rev. Biophys.* 1991, 24, 479–532. b) Michnicka, M. J.; Harper, J. W.; King, G. C. *Biochemistry* 1993, 32, 395–400.
9. a) Lancelot, G.; Chanteloup, L.; Beau, J.-M.; Thuong, N. T. *J. Am. Chem. Soc.* 1993, 115,1599–1600. b) Tate, S.; Ono, A.; Kainosho, M. *J. Am. Chem. Soc.* 1994, 116, 5977–78. c) Ono, A.; Tate, S.; Kainosho, M. *Tanpakushitsu Kakusan Koso* 1995, 40, 1509–17. d) Agrofoglio, L. A.; Jacquinet, J.-C.; Lancelot, G. *Tetrahedron Lett.* 1997, 38, 1411–12. e) Fernandez, C.; Szyperski, T.; Ono, A.; Iwai, H.; Tate, S.-i.; Kainosho, M.; Wuthrich K. *J Biomol. NMR* 1998, 12, 25–37. f) Pervushin, K.; Ono, A.; Fern‡ndez, C.; Szyperski, T.; Kainosho, M.; WŸthrich, K. *Proc. Natl. Acad. Sci. USA* 1998, 95, 14147–51.
10. Quant, S.; Weschelberger, R. W.; Wolter, M. A.; Wörner, K.-H.; Schell, P.; 20 Engels, J. W.; Griesinger, C.; Schwalbe, H. *Tetrahedron Lett.* 1994, 35, 6649–52.
11. a) Kupferschmitt, G.; Schmidt, J.; Schmidt, Th.; Fera, B.; Buck, F.; RŸterjans, H. *Nucleic Acids Res.* 1987, 15, 6225–40. b) Kellenbach, E. R.; Remerowski, M. L.; Eib, D.; Boelens, R.; van der Marel, G. A.; van den Elst, H.; van Boom, J. H.; Kaptein, R. *Nucleic Acids Res.* 1992, 20, 653–57. c) Jones, R. Stable Isotope *Applications in Biomolecular Structure and Mechanisms*; Trewhella, J., Cross, T. A., Unkefer, C. J. Eds.; Los Alamos National Laboratory: Los Alamos, 1994, 105–125.

12. Zimmer, D. P.; Crothers, D. M. *Proc. Natl. Acad. Sci. U.S.A.* 1995, 92, 3091–95.
13. Smith, D. E.; Su, J.-Y.; Jucker, F. M. *J. Biomol NMR* 1997, 10, 245–53.
14. Masse, J. E.; Bortman, P.; Dieckmann, T.; Feigon, J. *Nucleic Acids Res.* 1998, 26, 2618–24.
15. Louis, J. M.; Martin, R. G.; Clore, G. M.; Gronenborn, A. M. *J. Biol. Chem.* 1998, 273, 2374–78.
16. Chen, X.; Marriappan, S. V. S.; Kelly III, J. J.; Bushweller, J. H.; Bradbury, E. M.; Gupta, G. *FEBS Lett.* 1998, 436, 372–76.
17. a) Rudert, W. A.; Trucco, M. *Nucleic Acids Res.* 1990, 18, 6460. b) White, M. J.; Fristensky, B. W.; Thompson, W. F. *Anal Biochem.* 1991, 199,184–90. c) Hemat, F.; McEntee, K. *Biochem. Biophys. Res. Comm.* 1994, 205, 475–81.
18. Felli, I. C.; Richter, C.; Griesinger, C.; Schwalbe, H. *J. Am. Chem. Soc.* 1999, 121, 1956–1957.
19. Speck, N. A.; Stacy, T. Crit. *Rev. Eukary. Gene Express.* 1995, 5, 337–364.
20. (a) Ito, Y.; Bae, S.-C. In *Oncogenes as transcriptional regulators*, M. Yaniv and J. Ghysdael, eds. (Basel, Switzerland: BirkhauserVerlag), 1997, 2, 107–132. (b) Nagata, T.; Gupta, V.; Sorce, D.; Kim, W-Y.; Sali, A.; Chait, B. T.; Shigesada, K.; Ito, Y.; Werner, M. H. 1999 submitted.
21. Bustin, M.; Reeves, R. *Prog. Nuc. Acids Res. Mol. Biol.* 1996, 54, 35–100.
22. Bax, A.; Vuister, G. W.; Grzesiek, S.; Delaglio, F.; Wang, A. C.; Tschudin, R.; Zhu, G. *Meth. Enzymol.* 1994, 239, 79–106.
23. Dingley, A. J.; Grzesiek, S. *J. Am. Chem. Soc.* 1998, 120, 8293–8297.
24. Pervushin, K.; Ono, A.; Fernatndez, C.; Szyperski, T.; Kainosho, M.; WÿYthrich, K. *Proc. Natl. Acad. Sci. USA* 1998, 95,14147–14151.
25. Lu, C.; Erickson, H. P. Protein Express. Purif. 1997, 205, 475–81.
26. a) Bucurenci, N.; Sakamoto, H.; Briozzo, P.; Palibroda, N.; Serina, L.; Sarfati, R. S.; Labesse, G.; Briand, G.; Danchin, A.; B‰orzu, O.; Gilles, A.-M. *J. Biol. Chem.* 1996, 271, 2856–62. b) B‰orzu, O.; Michelson, S. *FEBS Lett.* 1983, 153, 280–284.
27. Mishra, N. C.; Broom, A. D. *J. Chem. Soc., Chem. Commun.* 1991, 1276.
28. Simon, E. S.; Grabowski, S.; Whitesides, G. M. *J. Org. Chem.* 1990, 55, 1834–41.
29. Vuister, G.; Bax, A. *J. Magn. Reson.* 1992, 98, 428–435.
30. Shaka, A. J.; Barker, P. B.; Freeman, R. *J. Magn. Reson.* 1985, 64, 547–552.
31. Grzesiek, S.; Bax, A. *J. Am. Chem. Soc.* 1993, 115, 12593–12594.
32. Wijmenga, S. S.; Mooren, M. M. W.; Hilbers, C. W. in *NMR of Macromolecules. A Practical Approach.* (ed. Roberts, G. C. K.) 1993, Oxford University Press, 217–288.
33. Marion, D.; Ikura, K.; Tschudin, R.; Bax, A. *J. Magn. Reson.* 1989, 85, 393–399.
34. Delaglio, F.; Grzesiek, S.; Vuister, G. W.; Zhu, G.; Pfeifer, J.; Bax, A. *J. Biomol. NMR* 1995, 6, 277–293.
35. Garrett, D. S.; Powers, R.; Gronenborn, A. M.; Clore, G. M. *J. Magn. Reson.* 1991, 95, 214–220.

What is claimed is:

1. A method for preparing a quantity of a duplex of a preselected polynucleotide sequence, said preselected polynucleotide sequence flanked by half of a preselected endonuclease cleavage site, said duplex of said preselected polynucleotide sequence capable of being produced after cleavage of a duplex tandem repeat of said preselected polynucleotide using said preselected endonuclease, said method comprising the steps of:

a) preparing a duplex tandem repeat and a quantity of single repeat of said preselected polynucleotide sequence;

b) amplifying said duplex tandem repeat by a DNA polymerase-catalyzed thermal amplification reaction in a first step comprising deoxynucleotide triphosphates, and producing a first product, said first step utilizing an optimized first annealing temperature selected by determining an annealing temperature which yields a maximal amount of preselected endonuclease-cleaved preselected polynucleotide sequence as a product of the first step;

c) amplifying said first product by a DNA polymerase-catalyzed thermal amplification reaction in a second step comprising deoxynucleotide triphosphates and a quantity of a single repeat of said preselected polynucleotide sequence, and producing a second product, said second step utilizing an optimized second annealing temperature selected by determining an annealing temperature which yields a maximal amount of endonuclease cleaved preselected polynucleotide sequence as a product of the second step; and d) cleaving said second product using said preselected endonuclease, producing said quantity of a duplex of said preselected polynucleotide sequence.

2. The method of claim 1 wherein said quantity of said single repeat of said preselected polynucleotide sequence is isotopically enriched.

3. The method of claim 1 wherein said half endonuclease site is selected from the group consisting of blunt-ended and overhanging.

4. The method of claim 1 wherein said deoxynucleotide triphosphates are isotopically enriched.

5. The method of claim 1 wherein said thermal amplification reaction is performed in a non-Peltier-type thermal cycler.

6. A method for preparing a quantity of a substantially pure duplex of a preselected polynucleotide sequence comprising isolating the duplex of said preselected polynucleotide sequence from the step (d) of claim 1.

7. The method of claim 1 wherein said duplex tandem repeat is prepared by solid-phase phosphoramidite chemistry.

8. The method of claim 1 wherein said preselected polynucleotide sequence is selected from the group consisting of an antisense oligonucleotide, duplex DNA, single-stranded DNA, triplex DNA, quadruplex DNA, 3-way junction DNA, and 4-way junction DNA.

9. The method of claim 4 wherein said isotopically enriched deoxynucleotide triphosphates are isotopically enriched with an atom selected from the group consisting of $^{13}C$, $^{15}N$, $^{2}H$, and combinations thereof.

10. The method of claim 4 wherein said isotopically enriched deoxynucleotide triphosphates are prepared by the enzymatic phosphorylation of deoxynucleotide phosphates obtained by digestion of nucleic acid isolated from an organism grown on a compound selected from the group consisting of an isotopically enriched carbon source, an isotopically enriched nitrogen source, an isotopically enriched hydrogen source, and any combination thereof.

11. The method of claim 6 wherein said isolation is carried out in a single-step chromatographic procedure.

12. The method of claim 10 wherein said enzymatic phosphorylation is achieved using thymidylate monophosphate kinase and cytidylate monophosphate kinase.

13. The method of claim 11 wherein said chromatographic procedure comprises DEAE ion-exchange HPLC.

14. A method for preparing a quantity of a substantially pure duplex of an isotopically enriched preselected polynucleotide sequence, said preselected polynucleotide sequence flanked by half of a preselected endonuclease cleavage site, said duplex of said preselected polynucleotide sequence capable of being produced after cleavage of a duplex tandem repeat of said preselected polynucleotide sequence using a preselected endonuclease, comprising the steps of:

a) preparing a duplex tandem repeat and a quantity of single repeat of said preselected polynucleotide sequence;

b) amplifying said duplex tandem repeat by a DNA polymerase-catalyzed thermal amplification reaction in a first step comprising isotopical enriched deoxynucleotide triphosphates, and producing a first product, said first step utilizing an optimized first annealing temperature;

c) amplifying said first product by a DNA polymerase-catalyzed thermal amplification reaction in a second step comprising isotopically enriched dNTPs, and a quantity of a single repeat of said preselected polynucleotide sequence, and producing a second product, said second step utilizing an optimized second annealing temperature;

d) cleaving said second product using said preselected endonuclease, producing a third product; and e) isolating said isotopically enriched duplex of said preselected polynucleotide sequence from said third product.

* * * * *